United States Patent
Okabe

(10) Patent No.: US 10,092,589 B2
(45) Date of Patent: Oct. 9, 2018

(54) ANTI-TUMOR AGENT CONTAINING ANTI-TUMOR PLATINUM COMPLEX, AND ANTI-TUMOR EFFECT ENHANCER

(71) Applicant: Taiho Pharmaceutical Company Limited, Tokyo (JP)

(72) Inventor: Hiroyuki Okabe, Ibaraki (JP)

(73) Assignee: Taiho Pharmaceutical Company Limited, Tokyo (JP)

( * ) Notice: Subject to any disclaimer, the term of this patent is extended or adjusted under 35 U.S.C. 154(b) by 0 days.

(21) Appl. No.: 15/301,807

(22) PCT Filed: Apr. 3, 2015

(86) PCT No.: PCT/JP2015/060635
§ 371 (c)(1),
(2) Date: Oct. 4, 2016

(87) PCT Pub. No.: WO2015/152407
PCT Pub. Date: Oct. 8, 2015

(65) Prior Publication Data
US 2017/0216339 A1 Aug. 3, 2017

(30) Foreign Application Priority Data

Apr. 4, 2014 (JP) .................................. 2014-078242
Feb. 10, 2015 (JP) .................................. 2015-024802

(51) Int. Cl.
| A61K 31/555 | (2006.01) |
| A61K 31/70 | (2006.01) |
| A61K 31/505 | (2006.01) |
| A61K 31/7072 | (2006.01) |
| A61K 31/513 | (2006.01) |
| A61K 33/24 | (2006.01) |

(52) U.S. Cl.
CPC ........ *A61K 31/7072* (2013.01); *A61K 31/513* (2013.01); *A61K 31/555* (2013.01); *A61K 33/24* (2013.01)

(58) Field of Classification Search
CPC .... A61K 33/24; A61K 31/7072; A61L 31/513
USPC .................. 514/50, 274, 184, 186; 424/649
See application file for complete search history.

(56) References Cited

U.S. PATENT DOCUMENTS

| 5,744,475 A | 4/1998 | Yano et al. |
| 2006/0167031 A1 | 7/2006 | Emura et al. |
| 2012/0130146 A1* | 5/2012 | Picard .................. A61K 31/675 600/1 |

FOREIGN PATENT DOCUMENTS

| WO | 9630346 A1 | 10/1996 |
| WO | 2010136168 A2 | 12/2010 |
| WO | 2012012404 A1 | 1/2012 |
| WO | 2013067165 A1 | 5/2013 |

OTHER PUBLICATIONS

International Search Report issued in corresponding International Application Ser. No. PCT/JP2015/060635, 2 pages, dated Jul. 7, 2015.
Temmink, O.H., et al., Mechanism of trifluorothymidine potentiation of oxaliplatin-induced cytotoxicity to colorectal cancer cells, Br. J. Cancer, vol. 96, No. 2, pp. 231-240, Jan. 23, 2007.
Overman, Michael J., et al., Phase 1 study of TAS-102 administered once daily on a 5-day-per-week schedule in patients with solid tumors; Invest New Drugs (2008) 26:445-454.
Yoshino, T., et al.; TAS-102 monotherapy for pretreated metastatic colorectal cancer: a double-blind, randomised, placebo-controlled phase 2 trial; Lancet Oncol. 13 (10): 993-1001, 2012.
Temmink, O.H., et al.; "Irinotecan-induced cytotoxicity to colon cancer cells in vitro is stimulated by pre-incubation with trifluorothymidine", Eur J Cancer, 43 (1): 175-83, 2007.
Bijnsdorp, I.V., et al., "Synergistic interaction between trifluorothymidine and docetaxel is sequence dependent", Cancer Sci. 99 (11): 2302-8, 2008.
Monneret, C., "Platinum anticancer drugs. From serendipity to rational design", Ann Pharm Fr. 2011: 69 (6): 286-95.
The English language translation of the International Preliminary Report on Patentability issued in corresponding International Application No. PCT/JP2015/060635, dated Oct. 18, 2016, 8 pages.
Supplementary European Search Report dated Nov. 10, 2017 in corresponding EP Application No. 15773963.2.
T. Emura et al., "Potentiation of the antitumor activity of a, a, a-trifluorothymidine by the co-administration of an inhibitor of thymidine phosphorylase at a suitable molar ration in vivo", International Journal of Oncology, vol. 27, pp. 449-455 (2005).
H. Yasui et al., "DNA synthesis inhibitors for the treatment of gastrointestinal cancer", Expert Opinion on Pharmacotherapy, 15(16), pp. 2361-2372 (2014).

(Continued)

*Primary Examiner* — Shengjun Wang
(74) *Attorney, Agent, or Firm* — Mintz Levin Cohn Ferris Glovsky and Popeo, P.C.; David G. Conlin; Joohee Lee

(57) ABSTRACT

In order to provide a novel cancer treatment method using a FTD•TPI combination drug that exhibits markedly excellent anti-tumor effects with fewer side effects, the present invention provides an anti-tumor agent characterized in that the FTD•TPI combination drug and an anti-tumor platinum complex are administered in combination.

8 Claims, 7 Drawing Sheets

(56) References Cited

OTHER PUBLICATIONS

A. Hollebecque et al., "A phase I dose-escalation of trifluridine/tipiracil in combination with oxaliplatin in metastatic colorectal cancer", Journal of Clinical Oncology, 35(15), 2017.

A. Hollebecque et al., "Phase I multicenter, open-label study to establish the maximum tolerated dose (MTD) of trifluridine/tipiracil (TAS-102) and oxaliplatin combination in patients (pts) with metastatic colorectal cancer (mCRC)", Journal of Clinical Oncology, 36(4), p. 816 (Feb. 2018).

* cited by examiner

ANTI-TUMOR AGENT CONTAINING ANTI-TUMOR PLATINUM COMPLEX, AND ANTI-TUMOR EFFECT ENHANCER

TECHNICAL FIELD

The present invention relates to an anti-tumor agent comprising a combination drug of trifluridine and tipiracil hydrochloride and an anti-tumor platinum complex and to an anti-tumor effect enhancer for an anti-tumor platinum complex.

BACKGROUND ART

Trifluridine (another name: α,α,α-trifluorothymidine; hereinafter also called "FTD") interferes with DNA synthesis by inhibition of thymidylate synthesis and interferes with DNA function by incorporation into DNA, thus exerting anti-tumor effects. Meanwhile, tipiracil hydrochloride (chemical name: 5-chloro-6-[(2-iminopyrrolidin-1-yl)methyl]pyrimidine-2,4(1H,3H)-dione hydrochloride; hereinafter also called "TPI") has a thymidine phosphorylase inhibitory effect. It is known that TPI suppresses in vivo degradation of FTD by thymidine phosphorylase, thus enhancing the anti-tumor effect of FTD (Patent Literature 1). At the present time, an anti-tumor agent comprising FTD and TPI at a molar ratio of 1:0.5 (hereinafter also called "FTD•TPI combination drug") has been developed as a therapeutic agent of solid cancers and is approved in Japan as a therapeutic agent for advanced or recurrent colorectal cancer (Non-Patent Literature 1 and 2).

In order to enhance the anti-tumor effect of the FTD•TPI combination drug, combination therapies have been studied, and the studies have suggested combination effects of the combination drug or FTD with irinotecan, oxaliplatin, docetaxel, or the like (Non-Patent Literature 3 to 5).

Anti-tumor platinum complexes are metal complex compounds containing platinum as the central metal, and inhibit DNA replication by binding to DNA, thus exerting anti-tumor effects. Platinum complexes as anti-tumor agents have been studied for a long time, and cisplatin, carboplatin, oxaliplatin, and the like are clinically used against a wide variety of cancer types (Non-Patent Literature 6). Combination use of anti-tumor platinum complexes with various anti-tumor agents has also been studied. In particular, combination use with an antimetabolite such as 5-fluorouracil is widely adopted.

CITATION LIST

Patent Literature

Patent Literature 1: International Publication WO 96/30346

Non-Patent Literature

Non-Patent Literature 1: Invest New Drugs 26 (5): 445-54, 2008.
Non-Patent Literature 2: Lancet Oncol. 13 (10): 993-1001, 2012.
Non-Patent Literature 3: Eur J Cancer. 43 (1): 175-83, 2007.
Non-Patent Literature 4: Br J Cancer. 96 (2): 231-40, 2007.
Non-Patent Literature 5: Cancer Sci. 99 (11): 2302-8, 2008.
Non-Patent Literature 6: Ann Pharm Fr. 2011; 69 (6): 286-95.

SUMMARY OF INVENTION

Technical Problem

The present invention has an object to provide a novel cancer treatment method using a FTD•TPI combination drug that exhibits markedly excellent anti-tumor effects with fewer side effects.

Solution to Problem

The present inventor has found that a FTD•TPI combination drug, which exhibits markedly excellent anti-tumor effects with acceptable side effects when used alone, surprisingly exhibits markedly enhanced anti-tumor effects without serious side effects when the FTD•TPI combination drug is used in combination with an anti-tumor platinum complex (especially cisplatin, carboplatin, and oxaliplatin), as compared with the case where either the FTD•TPI combination drug or the anti-tumor platinum complex is used alone.

Non-Patent Literature 4 discloses a combination use of FTD (TFT in Non-Patent Literature 4) and oxaliplatin but merely discloses in vitro combination tests, and there is no study about side effects. Hence, Non-Patent Literature 4 does not disclose whether the FTD•TPI combination drug and oxaliplatin can be actually administered in combination so as to exert anti-tumor effects with side effects being suppressed. In addition, Non-Patent Literature 4 does not disclose or suggest the preferred concentration ranges described in the present invention.

In other words, the present invention relates to the following aspects.

[1] An anti-tumor agent characterized in that an anti-tumor platinum complex and a combination drug containing trifluridine and tipiracil hydrochloride at a molar ratio of 1:0.5 are administered in combination.

[2] The anti-tumor agent according to the above [1], wherein a daily dose of the combination drug on an administration day of the combination drug is 50 to 100% of a recommended dose of the combination drug for use in monotherapy, and a daily dose of the anti-tumor platinum complex on an administration day of the anti-tumor platinum complex is 50 to 100% of a recommended dose of the anti-tumor platinum complex for use in monotherapy.

[3] The anti-tumor agent according to the above [1] or [2], wherein the anti-tumor platinum complex is cisplatin, carboplatin, or oxaliplatin.

[4] The anti-tumor agent according to any one of the above [1] to [3], wherein a daily dose of the combination drug on an administration day of the combination drug is 35 to 70 mg/m$^2$/day.

[5] The anti-tumor agent according to any one of the above [1] to [4], wherein a daily dose of cisplatin on an administration day of cisplatin is 45 to 90 mg/m$^2$/day.

[6] The anti-tumor agent according to any one of the above [1] to [4], wherein a daily dose of carboplatin on an administration day of carboplatin is 200 to 400 mg/m$^2$/day.

[7] The anti-tumor agent according to any one of the above [1] to [4], wherein a daily dose of oxaliplatin on an administration day of oxaliplatin is 65 to 130 mg/m$^2$/day.

[8] The anti-tumor agent according to any one of the above [1] to [7], wherein a target cancer is digestive cancer, lung cancer, or breast cancer.

[9] The anti-tumor agent according to any one of the above [1] to [8], wherein a target cancer is lung cancer.

[10] An anti-tumor effect enhancer for enhancing an anti-tumor effect of an anti-tumor platinum complex, the anti-tumor effect enhancer consisting of a combination drug containing trifluridine and tipiracil hydrochloride at a molar ratio of 1:0.5.

[11] An anti-tumor effect enhancer for enhancing an anti-tumor effect of a combination drug containing trifluridine and tipiracil hydrochloride at a molar ratio of 1:0.5, the anti-tumor effect enhancer consisting of an anti-tumor platinum complex.

[12] An anti-tumor agent for treating a cancer patient having received an anti-tumor platinum complex, the anti-tumor agent consisting of a combination drug containing trifluridine and tipiracil hydrochloride at a molar ratio of 1:0.5.

[13] An anti-tumor agent for treating a cancer patient having received a combination drug containing trifluridine and tipiracil hydrochloride at a molar ratio of 1:0.5, the anti-tumor agent consisting of an anti-tumor platinum complex.

[14] An anti-tumor agent consisting of a combination drug containing trifluridine and tipiracil hydrochloride at a molar ratio of 1:0.5, the anti-tumor agent being used in combination with an anti-tumor platinum complex.

[15] An anti-tumor agent consisting of an anti-tumor platinum complex, the anti-tumor agent being used in combination with a combination drug containing trifluridine and tipiracil hydrochloride at a molar ratio of 1:0.5.

[16] A kit preparation comprising:
an anti-tumor agent comprising a combination drug containing trifluridine and tipiracil hydrochloride at a molar ratio of 1:0.5; and
an instruction stating that the combination drug containing trifluridine and tipiracil hydrochloride at a molar ratio of 1:0.5 is administered in combination with an anti-tumor platinum complex to a cancer patient.

[17] A tumor treatment method comprising:
administering an anti-tumor platinum complex and a combination drug containing trifluridine and tipiracil hydrochloride at a molar ratio of 1:0.5, in combination to a mammal.

[18] The tumor treatment method according to the above [17], wherein a daily dose of the combination drug on an administration day of the combination drug is 50 to 100% of a recommended dose of the combination drug for use in monotherapy, and a daily dose of the anti-tumor platinum complex on an administration day of the anti-tumor platinum complex is 50 to 100% of a recommended dose of the anti-tumor platinum complex for use in monotherapy.

[19] The tumor treatment method according to the above [17] or [18], wherein the anti-tumor platinum complex is cisplatin, carboplatin, or oxaliplatin.

[20] The tumor treatment method according to any one of the above [17] to [19], wherein a daily dose of the combination drug on an administration day of the combination drug is 35 to 70 mg/m$^2$/day.

[21] The tumor treatment method according to any one of the above [17] to [20], wherein a daily dose of cisplatin on an administration day of cisplatin is 45 to 90 mg/m$^2$/day.

[22] The tumor treatment method according to any one of the above [17] to [20], wherein a daily dose of carboplatin on an administration day of carboplatin is 200 to 400 mg/m$^2$/day.

[23] The tumor treatment method according to any one of the above [17] to [20], wherein a daily dose of oxaliplatin on an administration day of oxaliplatin is 65 to 130 mg/m$^2$/day.

[24] The tumor treatment method according to any one of the above [17] to [23], wherein a target cancer is digestive cancer or lung cancer.

[25] The tumor treatment method according to any one of the above [17] to [23], wherein a target cancer is colorectal cancer, gastric cancer, or lung cancer.

[26] A method of enhancing an anti-tumor effect of an anti-tumor platinum complex, the method comprising:
administering an anti-tumor agent consisting of a combination drug containing trifluridine and tipiracil hydrochloride at a molar ratio of 1:0.5 to a mammal.

[27] A method of enhancing an anti-tumor effect of a combination drug containing trifluridine and tipiracil hydrochloride at a molar ratio of 1:0.5, the method comprising:
administering an anti-tumor agent consisting of an anti-tumor platinum complex to a mammal.

[28] A tumor treatment method for treating a cancer patient having received an anti-tumor platinum complex, the method comprising:
administering an anti-tumor agent consisting of a combination drug containing trifluridine and tipiracil hydrochloride at a molar ratio of 1:0.5 to the cancer patient.

[29] A tumor treatment method for treating a cancer patient having received a combination drug containing trifluridine and tipiracil hydrochloride at a molar ratio of 1:0.5, the method comprising:
administering an anti-tumor agent consisting of an anti-tumor platinum complex to the cancer patient.

[30] The anti-tumor agent according to any one of the above [1] to [9] for use in treating a tumor.

[31] The anti-tumor effect enhancer according to the above [10] or [11] for use in enhancing an anti-tumor effect.

[32] An anti-tumor agent consisting of a combination drug containing trifluridine and tipiracil hydrochloride at a molar ratio of 1:0.5, for use in treating a cancer patient having received an anti-tumor platinum complex.

[33] An anti-tumor agent consisting of an anti-tumor platinum complex for use in treating a cancer patient having received a combination drug containing trifluridine and tipiracil hydrochloride at a molar ratio of 1:0.5.

[34] Use of the anti-tumor agent according to any one of the above [1] to [9] for treating a tumor.

[35] Use of the anti-tumor effect enhancer according to the above [10] or [11] for enhancing an anti-tumor effect.

[36] Use of an anti-tumor agent consisting of a combination drug containing trifluridine and tipiracil hydrochloride at a molar ratio of 1:0.5, for treating a cancer patient having received an anti-tumor platinum complex.

[37] Use of an anti-tumor agent consisting of an anti-tumor platinum complex for treating a cancer patient having received a combination drug containing trifluridine and tipiracil hydrochloride at a molar ratio of 1:0.5. [38] Use of the anti-tumor agent according to any one of the above [1] to [9] for producing a medicine for treating a tumor.

[39] Use of the anti-tumor effect enhancer according to the above [10] or [11] for producing a medicine for enhancing an anti-tumor effect.

[40] Use of an anti-tumor agent consisting of a combination drug containing trifluridine and tipiracil hydrochloride at a molar ratio of 1:0.5, for producing a medicine for treating a cancer patient having received an anti-tumor platinum complex.

[41] Use of an anti-tumor agent consisting of an anti-tumor platinum complex for producing a medicine for treating a cancer patient having received a combination drug containing trifluridine and tipiracil hydrochloride at a molar ratio of 1:0.5.

Advantageous Effects of Invention

The present invention enables cancer treatment that achieves high anti-tumor effects (especially, tumor regression effect, tumor growth delay effect (life span increasing effect)) with side effects being suppressed. This enables cancer patients to live for a longer period of time.

DESCRIPTION OF EMBODIMENTS

Figure 1:
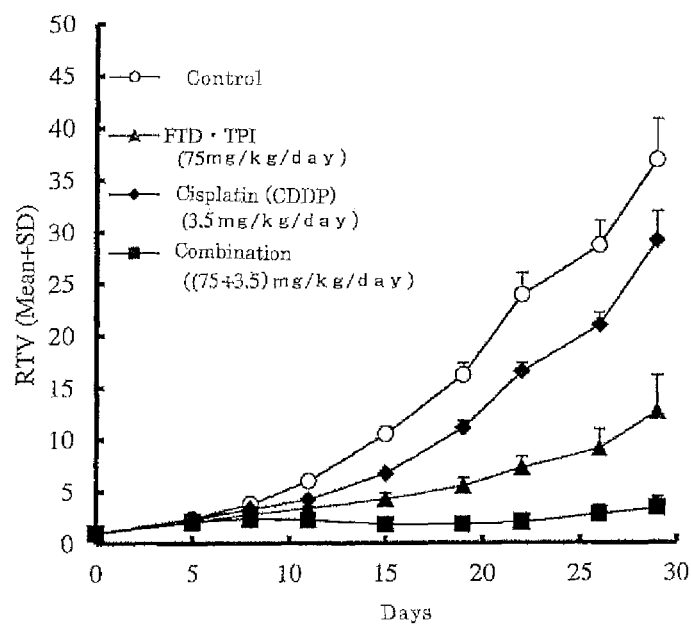
FIG. 1 is a view showing anti-tumor effects in mice having received the FTD•TPI combination drug (a molar ratio of FTD and TPI of 1:0.5) at a dose of 75 mg/kg/day in terms of FTD in combination with cisplatin at a dose of 3.5 mg/kg/day.
Figure 2:
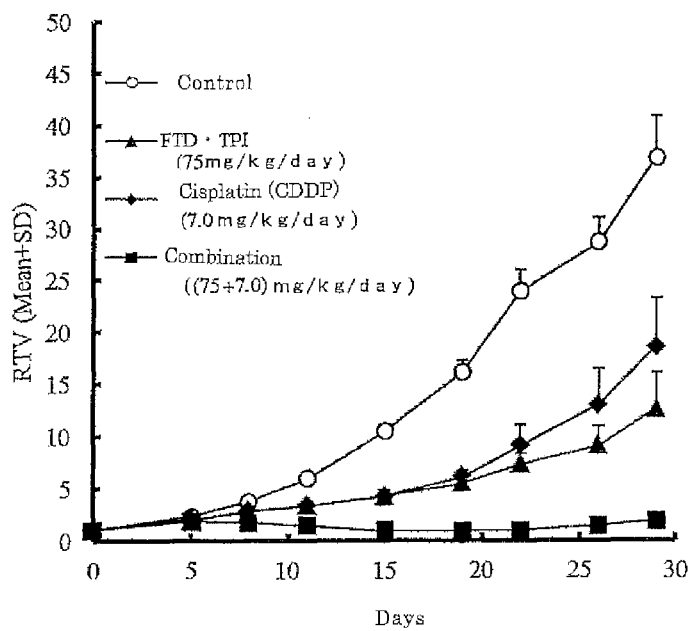
FIG. 2 is a view showing anti-tumor effects in mice having received the FTD•TPI combination drug (a molar ratio of FTD and TPI of 1:0.5) at a dose of 75 mg/kg/day in terms of FTD in combination with cisplatin at a dose of 7 mg/kg/day.
Figure 3:
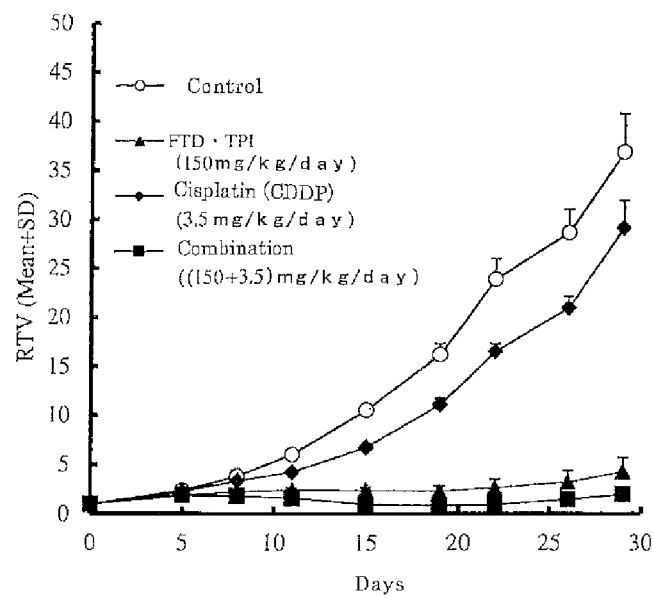
FIG. 3 is a view showing anti-tumor effects in mice having received the FTD•TPI combination drug (a molar ratio of FTD and TPI of 1:0.5) at a dose of 150 mg/kg/day in terms of FTD in combination with cisplatin at a dose of 3.5 mg/kg/day.
Figure 4:
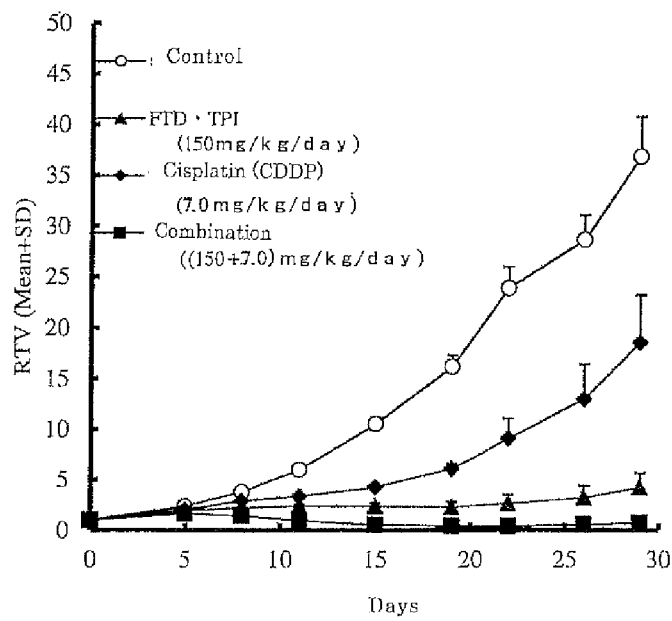
FIG. 4 is a view showing anti-tumor effects in mice having received the FTD•TPI combination drug (a molar ratio of FTD and TPI of 1:0.5) at a dose of 150 mg/kg/day of in terms of FTD in combination with cisplatin at a dose of 7 mg/kg/day.
Figure 5:
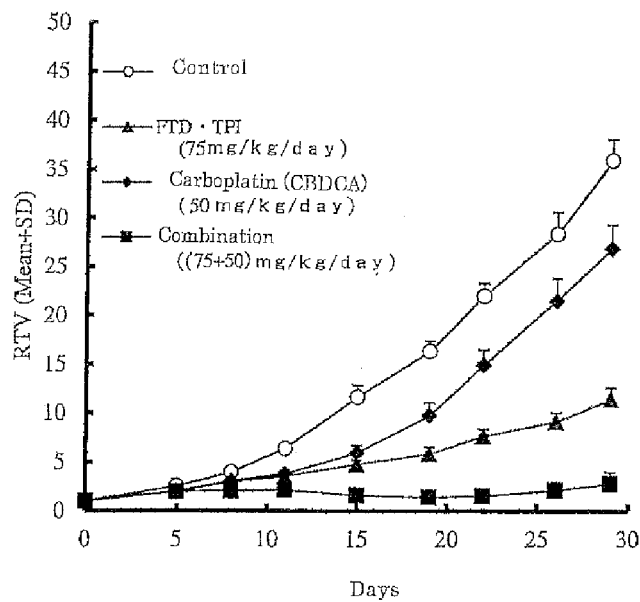
FIG. 5 is a view showing anti-tumor effects in mice having received the FTD•TPI combination drug (a molar ratio of FTD and TPI of 1:0.5) at a dose of 75 mg/kg/day in terms of FTD in combination with carboplatin at a dose of 50 mg/kg/day.
Figure 6:
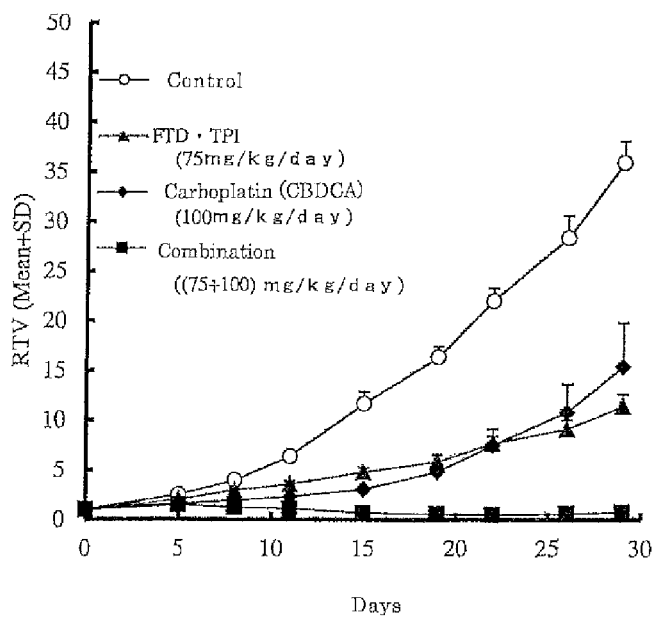
FIG. 6 is a view showing anti-tumor effects in mice having received the FTD•TPI combination drug (a molar ratio of FTD and TPI of 1:0.5) at a dose of 75 mg/kg/day in terms of FTD in combination with carboplatin at a dose of 100 mg/kg/day.
Figure 7:
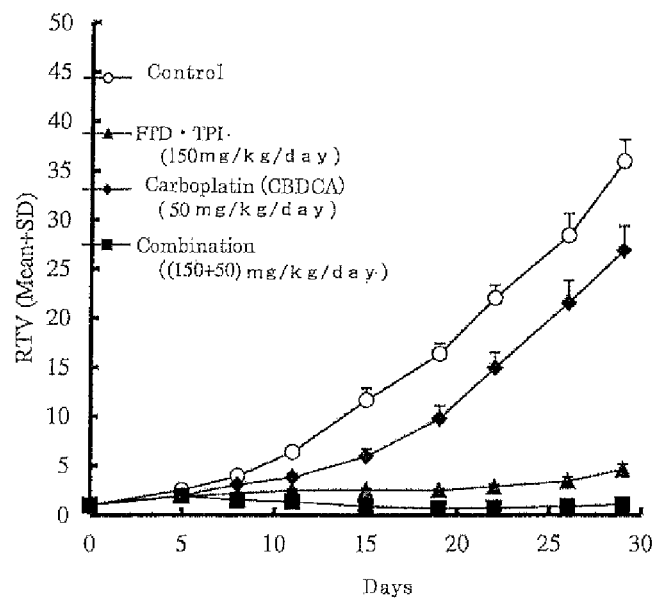
FIG. 7 is a view showing anti-tumor effects in mice having received the FTD•TPI combination drug (a molar ratio of FTD and TPI of 1:0.5) at a dose of 150 mg/kg/day in terms of FTD in combination with carboplatin at a dose of 50 mg/kg/day.
Figure 8:
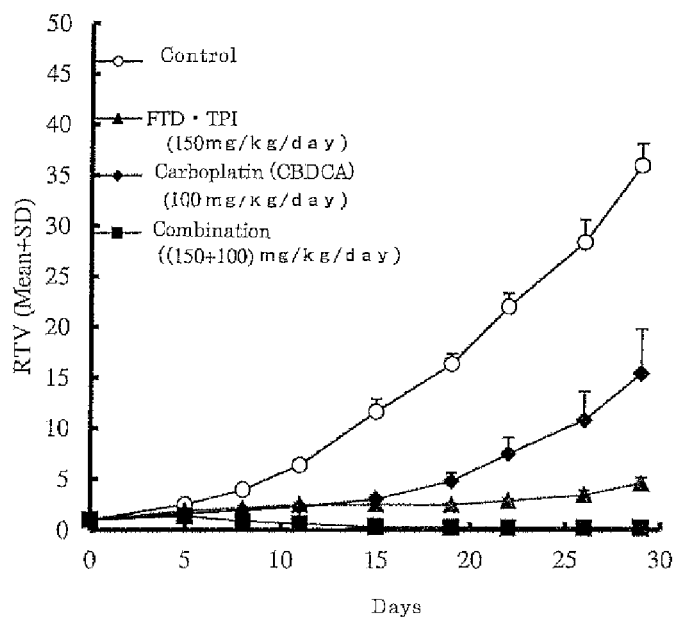
FIG. 8 is a view showing anti-tumor effects in mice having received the FTD•TPI combination drug (a molar ratio of FTD and TPI of 1:0.5) at a dose of 150 mg/kg/day in terms of FTD in combination with carboplatin at a dose of 100 mg/kg/day.

The present invention relates to an anti-tumor agent characterized in that a FTD•TPI combination drug and an anti-tumor platinum complex are administered in combination, an anti-tumor effect enhancer, use thereof, a tumor treatment method, and a method of enhancing an anti-tumor effect.

FTD and TPI, which are used in the present invention, are known compounds and can be synthesized by the methods disclosed in International Publication WO 96/30346, for example. A combination drug containing FTD and TPI at a molar ratio of 1:0.5 is also well-known (Non-Patent Literature 1 and 2). The FTD•TPI combination drug is approved in Japan as a therapeutic agent for advanced or recurrent colorectal cancer. The dosage regimen thereof is specified as follows: First, the combination drug is orally administered at a dose of 70 mg/m$^2$/day in terms of FTD twice a day for five consecutive days, and then a 2-day rest period is taken. This cycle is repeated twice, and then a 14-day rest period is taken. This is defined as one course, and the course is repeated.

The definition of the "anti-tumor platinum complex" in the present invention is part of common general technical knowledge, and the anti-tumor platinum complex may be any compound that has a platinum complex as the central metal and has anti-tumor activities. The anti-tumor platinum complex is specifically exemplified by cisplatin, carboplatin, oxaliplatin, and nedaplatin. Of them, preferred are cisplatin, carboplatin, and oxaliplatin, and particularly preferred are cisplatin and carboplatin. The anti-tumor platinum complex of the present invention includes drug delivery system (DDS) preparations containing the anti-tumor platinum complex as an active ingredient (for example, micellar cisplatin and liposomal oxaliplatin).

Cisplatin (chemical name: (SP-4-2)-diamminedichloroplatinum) is a known compound and can be synthesized by the method disclosed in JP-A No. 56-54233. Its commercial product (Randa inj. (registered trademark), Nippon Kayaku Co., Ltd.) can also be used.

Carboplatin (chemical name: cis-diammine (1,1-cyclobutanedicarboxylato)-platinum (II)) is a known compound and can be synthesized by the method disclosed in JP-B No. 56-29676. Its commercial product (Paraplatin inj. (registered trademark), Bristol-Myers) can also be used.

Oxaliplatin (chemical name: [(1R,2R)-cyclohexane-1,2-diamine](ethanedioato-O,O')platinum(II)) is a known compound and can be synthesized by the method disclosed in JP-B No. 7-76230. Its commercial product (Eloxatin (registered trademark), Sanofi-Aventis) can also be used.

In the present invention, the FTD•TPI combination drug can be administered to humans and other mammals (for example, rats, mice, rabbits, sheep, pigs, cows, cats, dogs, and monkeys). In the present invention, the anti-tumor platinum complex can be administered to humans and other mammals (for example, rats, mice, rabbits, sheep, pigs, cows, cats, dogs, and monkeys).

In the present invention, the daily dose of the FTD•TPI combination drug (a FTD:TPI molar ratio of 1:0.5) on an administration day is preferably 50 to 100% of a recommended dose of the FTD•TPI combination drug for use in monotherapy, and more preferably 100%, in view of the enhancement of the anti-tumor effects of an anti-tumor platinum complex by the FTD•TPI combination drug. Specifically, the recommended dose of the FTD•TPI combination drug for use in monotherapy in humans is 70 mg/m$^2$/day in terms of FTD, which is the dose approved in Japan as mentioned above. Accordingly, the daily dose of the FTD•TPI combination drug on an administration day is preferably 35 to 70 mg/m$^2$/day and more preferably 70 mg/m$^2$/day in terms of FTD in the present invention.

In the present invention, the "recommended dose" is a dose that is determined by clinical trials or the like and provides a maximum therapeutic effect within such a safety range as not to cause serious side effects. Specifically, the recommended dose includes doses that are approved, recommended, or advised by public institutions or groups including Japanese Pharmaceuticals and Medical Devices Agency (PMDA), U.S Food and Drug Administration (FDA), and European Medicines Agency (EMA) and are described on package inserts, interview forms, treatment guidelines, or the like. The recommended dose is preferably a dose approved by a public institution selected from PMDA, FDA, and EMA.

In the present invention, the daily dose of the anti-tumor platinum complex on an administration day is preferably 50 to 100% of a recommended dose of the anti-tumor platinum complex for use in monotherapy, and more preferably 100%, in view of the enhancement of the anti-tumor effects of the anti-tumor platinum complex by the FTD•TPI combination drug. Specifically, in accordance with the approved information on a package insert or an interview form, the recommended dose of cisplatin for use in monotherapy in humans on a five-consecutive-day schedule is 10 to 20 mg/m$^2$/day (for example, head and neck cancer, digestive cancer (including colorectal cancer and gastric cancer), lung cancer, breast cancer, ovarian cancer, cervical cancer, bladder cancer, prostate cancer, etc.; preferably head and neck cancer, digestive cancer, lung cancer, etc.), or 15 to 20 mg/m$^2$/day (for example, head and neck cancer, digestive cancer (including colorectal cancer and gastric cancer), lung cancer, breast cancer, ovarian cancer, cervical cancer, bladder cancer, prostate cancer, etc.; preferably digestive cancer, lung cancer, esophageal cancer, non-small cell lung cancer, ovarian cancer, cervical cancer, bladder cancer, and prostate cancer). Accordingly, when the recommended dose is 10 to 20 mg/m$^2$/day, the daily dose of cisplatin on an administration day is preferably 5 to 20 mg/m$^2$/day and more preferably 10 to 20 mg/m$^2$/day in the present invention. When the recommended dose is 15 to 20 mg/m$^2$/day, the daily dose of cisplatin on an administration day is preferably 7.5 to 20 mg/m$^2$/day, more preferably 10 to 20 mg/m$^2$/day, and particularly preferably 15 to 20 mg/m$^2$/day in the present invention.

In accordance with the approved information on a package insert or an interview form, the recommended dose of cisplatin for use in monotherapy in humans on a single-dosing schedule is 25 to 35 mg/m$^2$/day (for example, head and neck cancer, digestive cancer (including colorectal cancer and gastric cancer), lung cancer, breast cancer, ovarian cancer, cervical cancer, bladder cancer, prostate cancer, etc.; preferably digestive cancer, lung cancer, ovarian cancer, bladder cancer, and prostate cancer), 50 to 70 mg/m$^2$/day (for example, head and neck cancer, digestive cancer (including colorectal cancer and gastric cancer), lung cancer, breast cancer, ovarian cancer, cervical cancer, bladder cancer, prostate cancer, etc.; preferably digestive cancer, lung cancer, head and neck cancer, esophageal cancer, and ovarian cancer), or 70 to 90 mg/m$^2$/day (for example, head and neck cancer, digestive cancer (including colorectal cancer and gastric cancer), lung cancer, breast cancer, ovarian cancer, cervical cancer, bladder cancer, prostate cancer, etc.; preferably colorectal cancer, gastric cancer, non-small cell lung cancer, small cell lung cancer, and cervical cancer). Accordingly, when the recommended dose is 25 to 35 mg/m$^2$/day, the daily dose of cisplatin on an administration day is preferably 12.5 to 35 mg/m$^2$/day, more preferably 17.5 to 35 mg/m$^2$/day, and particularly preferably 25 to 35 mg/m$^2$/day in the present invention. When the recommended dose is 50 to 70 mg/m$^2$/day, the daily dose of cisplatin on an administration day is preferably 25 to 70 mg/m$^2$/day, more preferably 35 to 70 mg/m$^2$/day, and particularly preferably 50 to 70 mg/m$^2$/day in the present invention. When the recommended dose is 70 to 90 mg/m$^2$/day, the daily dose of cisplatin on an administration day is preferably 35 to 90 mg/m$^2$/day, more preferably 45 to 90 mg/m$^2$/day, and particularly preferably 70 to 90 mg/m$^2$/day in the present invention.

In accordance with the approved information on a package insert or an interview form, the recommended dose of carboplatin for use in monotherapy in humans on a once-every-four-week schedule (for example, head and neck cancer, digestive cancer (including colorectal cancer and gastric cancer), lung cancer, breast cancer, ovarian cancer, cervical cancer, bladder cancer, prostate cancer, etc.; preferably digestive cancer, head and neck cancer, non-small cell lung cancer, small cell lung cancer, ovarian cancer, and cervical cancer) is 300 to 400 mg/m$^2$/day. Accordingly, the daily dose of carboplatin on an administration day is preferably 150 to 400 mg/m$^2$/day, more preferably 200 to 400 mg/m$^2$/day, and particularly preferably 300 to 400 mg/m$^2$/day in the present invention.

In accordance with the approved information on a package insert or an interview form, the recommended dose of oxaliplatin for use in monotherapy in humans on a once-every-two-week schedule (for example, head and neck cancer, digestive cancer (including colorectal cancer and gastric cancer), lung cancer, breast cancer, ovarian cancer, cervical cancer, bladder cancer, prostate cancer, etc.; preferably colorectal cancer including colorectal cancer, gastric cancer, lung cancer, and pancreatic cancer) is 85 mg/m$^2$/day. Accordingly, the daily dose of oxaliplatin on an administration day is preferably 42.5 to 85 mg/m$^2$/day and more preferably 85 mg/m$^2$/day in the present invention. The recommended dose of oxaliplatin on a once-every-three-week schedule (for example, head and neck cancer, digestive cancer (including colorectal cancer and gastric cancer), lung cancer, breast cancer, ovarian cancer, cervical cancer, bladder cancer, prostate cancer, etc.; preferably colorectal cancer including colorectal cancer, gastric cancer, and lung cancer) is 130 mg/m$^2$/day. Accordingly, the daily dose of oxaliplatin on an administration day is preferably 65 to 130 mg/m$^2$/day and more preferably 130 mg/m$^2$/day in the present invention.

The administration schedule of the anti-tumor agent of the present invention can be appropriately determined depending on cancer types and disease stages, for example. The FTD•TPI combination drug is preferably administered on such an administration schedule that 5-day consecutive administration and a 2-day rest period are repeated twice and followed by a 2-week rest period or on such an administration schedule that 5-day consecutive administration and a 9-day rest period are repeated twice. Cisplatin is preferably administered on such an administration schedule that 5-day consecutive administration is followed by a rest period lasting at least 2 weeks or on such an administration schedule that 1-day administration is followed by a rest period lasting at least 3 weeks. Carboplatin is preferably administered on such an administration schedule that 1-day administration is followed by a rest period lasting at least 4 weeks. The above-described administration schedule may be repeated. A rest period may be provided depending on side effects and the like.

The daily administration frequency of the anti-tumor agent of the present invention can be appropriately determined depending on cancer types and disease stages, for example. The FTD•TPI combination drug is preferably administered twice a day, and the anti-tumor platinum complex is preferably administered once a day.

The order of the administration of the FTD•TPI combination drug and the anti-tumor platinum complex of the present invention can be appropriately determined depending on cancer types and disease stages, for example. Either one can be administered earlier, or both can be administered simultaneously.

The target cancer of the present invention is specifically exemplified by head and neck cancer, digestive cancer (for example, esophageal cancer, gastric cancer, duodenal cancer, liver cancer, biliary tract cancer (including gallbladder cancer and bile duct cancer), pancreatic cancer, small intestinal cancer, and colorectal cancer (including colorectal cancer, colon cancer, and rectal cancer)), lung cancer (non-small cell lung cancer and small cell lung cancer), breast cancer, ovarian cancer, uterine cancer (including cervical cancer and endometrial cancer), renal cancer, bladder cancer, and prostate cancer. Here, the cancer includes not only primary tumors but also metastatic cancers in other organs (for example, the liver). Of them, in view of anti-tumor effects and side effects, the target cancers are preferably head and neck cancer, digestive cancer, lung cancer, breast cancer, ovarian cancer, cervical cancer, bladder cancer, and prostate cancer, more preferably digestive cancer and lung cancer, even more preferably colorectal cancer, gastric cancer, and lung cancer, and particularly preferably colorectal cancer. The anti-tumor agent of the present invention may be used for postoperative adjuvant chemotherapy for recurrence prevention after surgical removal of tumors or used for preoperative adjuvant chemotherapy performed before surgical removal of tumors.

The administration schedules of the active ingredients are different, and hence the active ingredients cannot be mixed and formulated into a single preparation. The anti-tumor agent of the present invention is thus prepared in such a way that the active ingredients are formulated into a plurality of preparations. In other words, FTD and TPI are preferably formulated as a combination preparation, and the anti-tumor platinum complex is preferably formulated as a single preparation.

The plurality of preparations may be packed and sold in a single package suited for combination administration, or in separate packages as long as the active ingredients are administered at their respective doses specified in the present invention.

The dosage form of the anti-tumor agent of the present invention is not limited to particular forms and can be appropriately selected according to the therapeutic purpose. The dosage form is specifically exemplified by oral preparations (including tablets, coated tablets, powders, granules, capsules, and liquids), injections, suppositories, adhesive patches, and ointments. The combination drug of FTD and TPI is preferably prepared as an oral preparation. The anti-tumor platinum complex can be prepared in any of the above dosage forms and is preferably prepared in the form of an injection.

For the anti-tumor agent in the present invention, the FTD•TPI combination drug and the anti-tumor platinum complex single drug each can be prepared with the use of pharmaceutically acceptable carriers according to a known method appropriate for the dosage form. Such a carrier is exemplified by general purpose carriers commonly used in medicinal agents, such as excipients, binders, disintegrants, lubricants, diluents, solubilizing agents, suspending agents, tonicity agents, pH adjusters, buffers, stabilizers, coloring agents, flavoring agents, and odor improving agents.

The present invention also relates to an anti-tumor effect enhancer comprising a FTD•TPI combination drug for enhancing the anti-tumor effect of an anti-tumor platinum complex in cancer patients (especially, lung cancer patients and digestive cancer (including colorectal cancer and gastric cancer) patients). The anti-tumor effect enhancer can be prepared as any of the dosage forms mentioned for the above anti-tumor agent.

The present invention also relates to an anti-tumor effect enhancer comprising an anti-tumor platinum complex for enhancing the anti-tumor effect of a FTD•TPI combination drug in cancer patients (especially, lung cancer patients and, digestive cancer (including colorectal cancer and gastric cancer) patients). The anti-tumor effect enhancer can be prepared as any of the dosage forms mentioned for the above anti-tumor agent.

The present invention also relates to an anti-tumor agent comprising a FTD•TPI combination drug, for treating cancer patients (especially, lung cancer patients and digestive cancer (including colorectal cancer and gastric cancer) patients) having received an anti-tumor platinum complex. The anti-tumor agent can be prepared as any of the dosage forms mentioned above.

The present invention also relates to an anti-tumor agent comprising an anti-tumor platinum complex, for treating cancer patients (especially, lung cancer patients and digestive cancer (including colorectal cancer and gastric cancer) patients) having received a FTD•TPI combination drug. The anti-tumor agent can be prepared as any of the dosage forms mentioned above.

The present invention also relates to an anti-tumor agent comprising a FTD•TPI combination drug, and the anti-tumor agent is administered in combination with an anti-tumor platinum complex to cancer patients (especially, lung cancer patients and digestive cancer (including colorectal cancer and gastric cancer) patients). The anti-tumor agent can be prepared as any of the dosage forms mentioned above.

The present invention also relates to an anti-tumor agent comprising an anti-tumor platinum complex, and the anti-tumor agent is administered in combination with a FTD•TPI combination drug to cancer patients (especially, lung cancer patients and digestive cancer (including colorectal cancer and gastric cancer) patients). The anti-tumor agent can be prepared as any of the dosage forms mentioned above.

The present invention also relates to a kit preparation comprising a FTD•TPI combination drug and an instruction stating that the FTD•TPI combination drug is administered in combination with an anti-tumor platinum complex to cancer patients (especially, lung cancer patients and digestive cancer (including colorectal cancer and gastric cancer) patients). Here, the "instruction" may be any instruction that states the above doses, but is preferably an instruction that recommends the above doses whether such recommendation is legally binding or not. The instruction is specifically exemplified by package inserts and pamphlets. The kit preparation comprising an instruction may be provided in a package on which the instruction is printed or attached or in a package in which the instruction is packed together with the anti-tumor agent.

The present invention also relates to a tumor treatment method that comprises administering an anti-tumor platinum complex and a combination drug containing trifluridine and tipiracil hydrochloride at a molar ratio of 1:0.5 in combination to mammals.

The present invention also relates to a method of enhancing the anti-tumor effect of an anti-tumor platinum complex, and the method comprises administering an anti-tumor agent consisting of a combination drug containing trifluridine and tipiracil hydrochloride at a molar ratio of 1:0.5 to mammals.

The present invention also relates to a method of enhancing the anti-tumor effect of a combination drug containing trifluridine and tipiracil hydrochloride at a molar ratio of 1:0.5, and the method comprises administering an anti-tumor agent consisting of an anti-tumor platinum complex to mammals.

The present invention also relates to a tumor treatment method for treating a cancer patient having received an anti-tumor platinum complex, and the method comprises administering an anti-tumor agent consisting of a combination drug containing trifluridine and tipiracil hydrochloride at a molar ratio of 1:0.5 to the cancer patient.

The present invention also relates to a tumor treatment method for treating a cancer patient having received a combination drug containing trifluridine and tipiracil hydrochloride at a molar ratio of 1:0.5, and the method comprises administering an anti-tumor agent consisting of an anti-tumor platinum complex to the cancer patient.

The present invention also relates to the anti-tumor agent of the present invention for use in treating a tumor.

The present invention also relates to the anti-tumor effect enhancer of the present invention for use in enhancing an anti-tumor effect.

The present invention also relates to an anti-tumor agent consisting of a combination drug containing trifluridine and tipiracil hydrochloride at a molar ratio of 1:0.5, for use in treating a cancer patient having received an anti-tumor platinum complex.

The present invention also relates to an anti-tumor agent consisting of an anti-tumor platinum complex for use in treating a cancer patient having received a combination drug containing trifluridine and tipiracil hydrochloride at a molar ratio of 1:0.5.

The present invention also relates to use of the anti-tumor agent of the present invention for treating a tumor.

The present invention also relates to use of the anti-tumor effect enhancer of the present invention for enhancing an anti-tumor effect.

The present invention also relates to use of an anti-tumor agent consisting of a combination drug containing trifluridine and tipiracil hydrochloride at a molar ratio of 1:0.5, for treating a cancer patient having received an anti-tumor platinum complex.

The present invention also relates to use of an anti-tumor agent consisting of an anti-tumor platinum complex for treating a cancer patient having received a combination drug containing trifluridine and tipiracil hydrochloride at a molar ratio of 1:0.5.

The present invention also relates to use of the anti-tumor agent of the present invention for producing a medicine for treating a tumor.

The present invention also relates to use of the anti-tumor effect enhancer of the present invention for producing a medicine for enhancing an anti-tumor effect.

The present invention also relates to use of an anti-tumor agent consisting of a combination drug containing trifluridine and tipiracil hydrochloride at a molar ratio of 1:0.5, for producing a medicine for treating a cancer patient having received an anti-tumor platinum complex.

The present invention also relates to use of an anti-tumor agent consisting of an anti-tumor platinum complex for producing a medicine for treating a cancer patient having received a combination drug containing trifluridine and tipiracil hydrochloride at a molar ratio of 1:0.5.

EXAMPLES

The present invention will next be described in more detail with reference to examples and reference examples, but the present invention is not intended to be limited by these examples. Many modifications can be made by a person skilled in the art within the technical ideas of the present invention.

Reference Example 1

Cultured cells ($1 \times 10^7$ cells/mouse) of a human colon cancer cell line (KM20C) were transplanted into the abdominal cavity of 5 to 6-week-old BALB/cA Jcl-nu mice. The mice were divided into groups (n=10) in such a way that each group had an equal mean body weight, and the grouping day was defined as Day 0.

A FTD•TPI combination drug (a mixture of FTD and TPI at a molar ratio of 1:0.5) was prepared for administration at doses of 75, 100, 150, 300, and 450 mg/kg/day in terms of FTD. The administration of the drug was started from. Day 3. The FTD•TPI combination drug was orally administered for five consecutive days and then a 2-day rest period was taken. This cycle was repeated for 6 weeks.

As an index of the anti-tumor effect, the number of living mice was counted in each group, and the life spans and the increased life spans of the groups were compared. The increased life span (ILS) was calculated in accordance with the following equation.

$$ILS(\%) = [\{(\text{mean life span of administered group})/(\text{mean life span of control group})\} - 1] \times 100$$

Table 1 shows the results.

TABLE 1

| Group | Dose (mg/kg/day in terms of FTD) | Mean life span (day) Mean ± SD | ILS (%) |
|---|---|---|---|
| Control | — | 40.0 ± 4.3 | — |
| FTD·TPI combination | 75 | 50.0 ± 9.1 | 25.0 |
| FTD·TPI combination | 100 | 75.8 ± 42.6 | 89.5 |

TABLE 1-continued

| Group | Dose (mg/kg/day in terms of FTD) | Mean life span (day) Mean ± SD | ILS (%) |
|---|---|---|---|
| FTD·TPI combination | 150 | 125.7 ± 64.8 | 214.3 |
| FTD·TPI combination | 300 | 75.6 ± 17.5 | 89.0 |
| FTD·TPI combination | 450 | 54.1 ± 18.3 | 35.3 |

As shown in Table 1, the FTD•TPI combination drug showed life span increasing effect in all the groups at 75 to 450 mg/kg/day in terms of FTD. Of them, the group at 150 mg/kg/day showed a maximum life span. Thus, the recommended dose (RD) of the FTD•TPI combination drug for mice is 150 mg/kg/day in terms of FTD. In other words, the results indicate that the FTD•TPI combination drug exerts the life span increasing effect at least at a dose of 50% to 300% of the RD.

Meanwhile, it is known that the RD of the FTD•TPI combination drug for use in monotherapy in humans is 70 mg/m$^2$/day in terms of FTD. Accordingly, as for the dose of the FTD•TPI combination drug in terms of FTD, 150 mg/kg/day for mice corresponds to 70 mg/m$^2$/day for humans.

Reference Example 2

To BALB/cA Jcl-nu mice (8 mice in each group) to which a human colon cancer cell line KM20C had been transplanted, cisplatin was administered through the tail vein on Day 1 and Day 8. At a dose of 7 mg/kg/day, body weight reduction was 20% or less, and this dose was feasible. Accordingly, the recommended dose of cisplatin (CDDP) for mice was 7 mg/kg/day.

Reference Example 3

To BALB/cA Jcl-nu mice with no cancer (5 mice in each group), carboplatin (CBDCA) was administered at 50, 70, 100, 140, or 200 mg/kg/day through the tail vein on Day 1. In the groups treated with the doses of 140 mg/kg/day or more, strong body weight reductions of 20% or more and death cases were observed. The recommended dose of carboplatin for mice was thus 100 mg/kg/day.

Reference Example 4

To BALB/cA Jcl-nu mice with no cancer (4 mice in each group), oxaliplatin (l-OHP) was administered at 10, 12, 15, or 22.5 mg/kg/day through the tail vein on Day 1 and Day 8. In the groups treated with the doses of 15 mg/kg/day or more, strong body weight reductions of 20% or more were observed. The recommended dose of oxaliplatin for mice was thus 12 mg/kg/day.

Example 1: Combination Use of FTD•TPI Combination Drug and Cisplatin

A human lung cancer cell line (Lu-134) was transplanted to the right chest of 5 to 6-week-old BALB/cA Jcl-nu mice. After the tumor transplantation, the long diameter (mm) and the short diameter (mm) of the tumor were measured, and the tumor volume (TV) was calculated. The mice were divided into groups (n=6) in such a way that each group had an equal mean TV, and the grouping day was defined as Day 0.

The FTD•TPI combination drug (a mixture of FTD and TPI at a molar ratio of 1:0.5) was prepared for administration at doses of 75 and 150 mg/kg/day in terms of FTD. Cisplatin (Randa inj., Nippon Kayaku Co., Ltd) was prepared for administration at doses of 3.5 and 7 mg/kg/day. The FTD•TPI combination drug was orally administered on Days 1 to 14 consecutively, and cisplatin was administered through the tail vein on Day 1 and Day 8. In the combination administration groups, the doses and administration schedules of the FTD•TPI combination drug and cisplatin were the same as those of the corresponding monotherapy groups.

As an index of the anti-tumor effect, the TVs on Days 5, 8, 11, 15, 19, 22, 26, and 29 were calculated in each group. In accordance with the following equation, the relative tumor volume (RTV) to that on Day 0 was calculated and compared with the RTV of the untreated group (control). The combination effect was evaluated as follows: when the mean RTV value of a combination administration group is statistically, significantly smaller (closed testing procedure; intersection-union test, p<0.01) than those of the corresponding monotherapy groups, the combination administration was regarded as having an enhancement effect.

The results are shown in Table.

$$TV(mm^3)=(\text{long diameter} \times \text{short diameter}^2)/2$$

$$RTV=(TV \text{ on Day } 29)/(TV \text{ on Day } 0)$$

The RTVs were plotted on the indicated measurement days, and RTV changes over days in the control group, the FTD•TPI combination drug administration group, the cisplatin administration group, and the combination administration group of the FTD•TPI combination drug and cisplatin were compared.

The tumor growth inhibition rate (IR) on Day 29 on the basis of RTV values was calculated in accordance with the following equation.

$$IR(\%)=[1-(\text{mean } RTV \text{ value of treated group})/(\text{mean } RTV \text{ value of control group})] \times 100$$

The results of the groups on Day 29 are shown in Table 2.

To evaluate body weight reduction as an index of side effects, body weights were measured in each group on each measurement day.

TABLE 2

| Drug | Dose (mg/kg/day) | RTV[a] (mean ± SD) | IR[b] (%) |
|---|---|---|---|
| Control | — | 36.84 ± 3.94 | — |
| FTD·TPI combination | 75 | 12.63 ± 3.48** | 65.7 |
| FTD·TPI combination | 150 | 4.24 ± 1.42** | 88.5 |
| Cisplatin (CDDP) | 3.5 | 29.12 ± 2.79** | 21.0 |
| Cisplatin (CDDP) | 7.0 | 18.56 ± 4.64** | 49.6 |
| FTD·TPI combination + CDDP | 75 + 3.5 | 3.35 ± 1.08**## | 90.9 |
| FTD·TPI combination + CDDP | 75 + 7.0 | 1.87 ± 0.79**## | 94.9 |
| FTD·TPI combination + CDDP | 150 + 3.5 | 1.98 ± 0.40**## | 94.6 |
| FTD·TPI combination + CDDP | 150 + 7.0 | 0.74 ± 0.38**## | 98.0 |

**p < 0.01 vs. Control by Dunnett's test.
overall maximal p < 0.01 by closed testing procedure (Intersection-Union Test), respectively.
[a]Relative tumor volume (RTV) on Day 29 was calculated as the ratio of TV on Day 29 to that on Day 0 according to the following formula: RTV = (TV on Day 29)/(TV on Day 0)
[b]Tumor growth inhibition rate (IR) on Day 29 on the basis of RTV was calculated according to the following formula: IR (%) = [1 − (mean RTV of the treated group)/(mean RTV of the control group)] × 100

As shown in Table 2 and FIGS. 1 to 4, statistically significantly enhanced anti-tumor effects were observed when the FTD•TPI combination drug was administered at 75 to 150 mg/kg/day in terms of FTD and cisplatin was administered at 3.5 to 7 mg/kg/day. In the combination administration groups of the FTD•TPI combination drug and cisplatin, no serious body weight reduction (more than 20% reduction) was observed, and side effects were acceptable.

As shown in Reference Examples, the recommended dose of the FTD•TPI combination drug for use in monotherapy is 150 mg/kg/day (in terms of FTD), and the recommended dose of cisplatin for use in monotherapy is 7 mg/kg/day. This indicates that a marked enhancement of the anti-tumor effect was observed when the FTD•TPI combination drug was administered at 50 to 100% of the recommended dose for use in monotherapy and cisplatin was administered at 50 to 100% of the recommended dose for use in monotherapy.

Example 2: Combination Use of FTD•TPI Combination Drug and Carboplatin

In a similar manner to that in Example 1, to BALB/cA Jcl-nu mice to which a human lung cancer cell line (Lu-134) had been transplanted, the FTD•TPI combination drug or carboplatin alone, or a combination of the two was administered, and enhancement of the anti-tumor effect was examined.

The FTD•TPI combination drug (a mixture of FTD and TPI at a molar ratio of 1:0.5) was prepared for administration at doses of 75 and 150 mg/kg/day in terms of FTD. Carboplatin (Paraplatin inj., Bristol-Myers) was prepared for administration at doses of 50 and 100 mg/kg/day. The FTD•TPI combination drug was orally administered on Days 1 to 14 consecutively, and carboplatin was administered through the tail vein on Day 1 and Day 8. In the combination administration groups, the doses and administration schedules of the FTD•TPI combination drug and carboplatin were the same as those of the corresponding monotherapy groups. The TV and body weight of each group were measured on Days 4, 8, 11, 15, 19, 22, 26, and 29, and the anti-tumor effect and side effects were evaluated. The results of the groups on Day 29 are shown in Table 3.

TABLE 3

| Drug | Dose (mg/kg/day) | RTV[a] (mean ± SD) | IR[b] (%) |
|---|---|---|---|
| Control | — | 35.94 ± 2.16 | — |
| FTD·TPI combination | 75 | 11.40 ± 1.19** | 68.3 |
| FTD·TPI combination | 150 | 4.59 ± 0.53** | 87.2 |
| Carboplatin (CBDCA) | 50 | 26.86 ± 2.44** | 25.3 |
| Carboplatin (CBDCA) | 100 | 15.40 ± 4.38** | 57.2 |
| FTD·TPI combination + CBDCA | 75 + 50 | 2.78 ± 1.18**,## | 92.3 |
| FTD·TPI combination + CBDCA | 75 + 100 | 0.72 ± 0.66**,## | 98.0 |
| FTD·TPI combination + CBDCA | 150 + 50 | 1.03 ± 0.51**,## | 97.1 |
| FTD·TPI combination + CBDCA | 150 + 100 | 0.18 ± 0.18**,## | 99.5 |

**p < 0.01 vs. Control by Dunnett's test.
overall maximal p < 0.01 by closed testing procedure (Intersection-Union Test), respectively.
[a]Relative tumor volume (RTV) on Day 29 was calculated as the ratio of TV on Day 29 to that on Day 0 according to the following formula: RTV = (TV on Day 29)/(TV on Day 0)
[b]Tumor growth inhibition rate (IR) on Day 29 on the basis of RTV was calculated according to the following formula: IR (%) = [1 − (mean RTV of the treated group)/(mean RTV of the control group)] × 100

As shown in Table 3 and FIGS. 5 to 8, statistically significantly enhanced anti-tumor effects were observed when the FTD•TPI combination drug was administered at 75 to 150 mg/kg/day in terms of FTD and carboplatin was administered at 50 to 100 mg/kg/day. In the combination administration groups of the FTD•TPI combination drug and carboplatin, no serious body weight reduction (more than 20% reduction) was observed, and side effects were acceptable.

As shown in Reference Examples, the recommended dose of the FTD•TPI combination drug for use in monotherapy is 150 mg/kg/day (in terms of FTD), and the recommended dose of carboplatin for use in monotherapy is 100 mg/kg/day. This indicates that a marked enhancement of the anti-tumor effect was observed when the FTD•TPI combination drug was administered at 50 to 100% of the recommended dose for use in monotherapy and carboplatin was administered at 50 to 100% of the recommended dose for use in monotherapy.

Example 3-1: Combination Use of FTD•TPI Combination Drug and Oxaliplatin

In a similar manner to that in Example 1, to BALB/cA Jcl-nu mice to which a human colon cancer cell strain (KM20C) had been transplanted, the FTD•TPI combination drug or oxaliplatin alone, or a combination of the two was administered, and enhancement of the anti-tumor effect was examined.

The FTD•TPI combination drug (a mixture of FTD and TPI at a molar ratio of 1:0.5) was prepared for administration at doses of 75 and 150 mg/kg/day in terms of FTD. Oxaliplatin (Eloxatin, Sanofi-Aventis) was prepared for administration at doses of 6 and 12 mg/kg/day. The FTD•TPI combination drug was orally administered on Days 1 to 14 consecutively, and oxaliplatin was administered through the tail vein on Day 1 and Day 8. In the combination administration groups, the doses and administration schedules of the FTD•TPI combination drug and oxaliplatin were the same as those of the corresponding monotherapy groups. The TV and body weight of each group were measured on Days 4, 7, 10, and 15, and the anti-tumor effect and side effects were evaluated. The results of the groups on Day 15 are shown in Table 4.

TABLE 4

| Drug | Dose (mg/kg/day) | RTV[a] (mean ± SD) | IR[b] (%) |
|---|---|---|---|
| Control | — | 10.98 ± 0.88 | — |
| FTD·TPI combination | 75 | 6.18 ± 0.31** | 43.7 |
| FTD·TPI combination | 150 | 4.64 ± 0.24** | 57.8 |
| Oxaliplatin (l-OHP) | 6 | 6.99 ± 0.32** | 36.4 |
| Oxaliplatin (l-OHP) | 12 | 4.94 ± 0.53** | 55.0 |
| FTD·TPI combination + l-OHP | 75 + 6 | 4.50 ± 0.21**,## | 59.0 |
| FTD·TPI combination + l-OHP | 75 + 12 | 3.89 ± 0.20**,## | 64.5 |
| FTD·TPI combination + l-OHP | 150 + 6 | 3.54 ± 0.22**,## | 67.8 |
| FTD·TPI combination + l-OHP | 150 + 12 | 2.72 ± 0.17**,## | 75.2 |

**p < 0.01 vs. Control by Dunnett's test.
overall maximal p < 0.01 by closed testing procedure (Intersection-Union Test), respectively.
[a]Relative tumor volume (RTV) on Day 15 was calculated as the ratio of TV on Day 15 to that on Day 0 according to the following formula: RTV = (TV on Day 15)/(TV on Day 0)
[b]Tumor growth inhibition rate (IR) on Day 15 on the basis of RTV was calculated according to the following formula: IR (%) = [1 − (mean RTV of the treated group)/(mean RTV of the control group)] × 100

As shown in Table 4, statistically significantly enhanced anti-tumor effects were observed when the FTD•TPI combination drug was administered at 75 to 150 mg/kg/day in terms of FTD and oxaliplatin was administered at 6 to 12 mg/kg/day. In the combination administration groups of the FTD•TPI combination drug and oxaliplatin, no serious body weight reduction (more than 20% reduction) was observed, and side effects were acceptable.

As shown in Reference Examples, the recommended dose of the FTD•TPI combination drug for use in monotherapy is 150 mg/kg/day (in terms of FTD), and the recommended dose of oxaliplatin for use in monotherapy is 12 mg/kg/day. This indicates that a marked enhancement of the anti-tumor effect was observed when the FTD•TPI combination drug was administered at 50 to 100% of the recommended dose for use in monotherapy and oxaliplatin was administered at 50 to 100% of the recommended dose for use in monotherapy.

Example 3-2: Combination Use of FTD•TPI Combination Drug and Oxaliplatin

In a similar manner to that in Example 1, to BALB/cA Jcl-nu mice to which a human colon cancer cell strain (SW48) had been transplanted, the FTD•TPI combination drug or oxaliplatin alone, or a combination of the two was administered, and enhancement of the anti-tumor effect was examined.

The FTD•TPI combination drug (a mixture of FTD and TPI at a molar ratio of 1:0.5) was prepared for administration at a dose of 150 mg/kg/day in terms of FTD. Oxaliplatin (Eloxatin, Sanofi-Aventis) was prepared for administration at doses of 7 and 12 mg/kg/day. The FTD•TPI combination drug was orally administered on Days 1 to 14 consecutively, and oxaliplatin was administered through the tail vein on Day 1 and Day 8. In the combination administration groups, the doses and administration schedules of the FTD•TPI combination drug and oxaliplatin were the same as those of the corresponding monotherapy groups. The TV and body weight of each group were measured on Days 3, 7, 11, 15, 18, 22, 25, and 29, and the anti-tumor effect and side effects were evaluated. The results of the groups on Day 29 are shown in Table 5.

As shown in Reference Examples, the recommended dose of the FTD•TPI combination drug for use in monotherapy is 150 mg/kg/day (in terms of FTD), and the recommended dose of oxaliplatin for use in monotherapy is 12 mg/kg/day. This indicates that a marked enhancement of the anti-tumor effect was observed when the FTD•TPI combination drug was administered at 100% of the recommended dose for use in monotherapy and oxaliplatin was administered at 58 to 100% of the recommended dose for use in monotherapy.

TABLE 5

| Group | Dose (mg/kg/day) | RTV[a] (mean ± SD) | IR[b] (%) | RTV5[c] (days) |
|---|---|---|---|---|
| Control | — | 61.14 ± 5.70 | — | 6.7 ± 0.4 |
| FTD-TPI | 150 | 19.57 ± 2.96* | 68.0 | 9.4 ± 0.5$ |
| Oxaliplatin | 7 | 47.63 ± 4.33 | 22.1 | 8.9 ± 0.4 |
| (l-OHP) | 12 | 38.72 ± 3.69*,# | 36.7 | 10.0 ± 0.8$ |
| Combination | 150 + 7 | 12.28 ± 1.04*,# | 79.9 | 13.4 ± 1.7$,& |
|  | 150 + 12 | 8.70 ± 0.64*,# | 85.8 | 15.6 ± 2.6$,& |

*$P < 0.001$ vs. Control using two-sided Aspin-Welch t-test.
$P < 0.001$ by closed testing procedure using two-sided Aspin-Welch t-test.
$$P < 0.001$ vs. Control using Log-rank test.
&$P < 0.001$ vs. either monotherapy using Log-rank test.
[a]Relative tumor volume (RTV) on Day 29 was calculated as the ratio of TV on Day 29 to that on Day 0 according to the following formula: RTV = (TV on Day 29)/(TV on Day 0)
[b]Tumor growth inhibition rate (IR) on Day 29 on the basis of RTV was calculated according to the following formula: IR (%) = [1 − (mean RTV of the treated group)/(mean RTV of the control group)] × 100
[c]The period, RTV reaches 5

Figure 9:
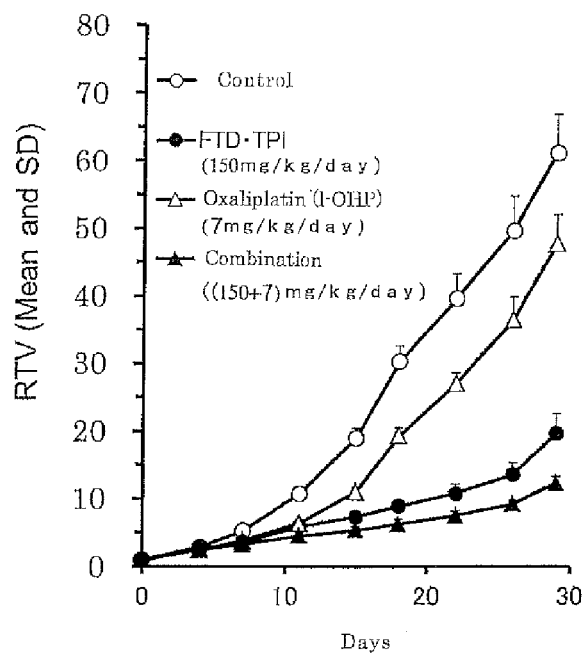
FIG. 9 is a view showing anti-tumor effects in mice having received the FTD•TPI combination drug (a molar ratio of FTD and TPI of 1:0.5) at a dose of 150 mg/kg/day in terms of FTD in combination with oxaliplatin at a dose of 7 mg/kg/day.
Figure 10:
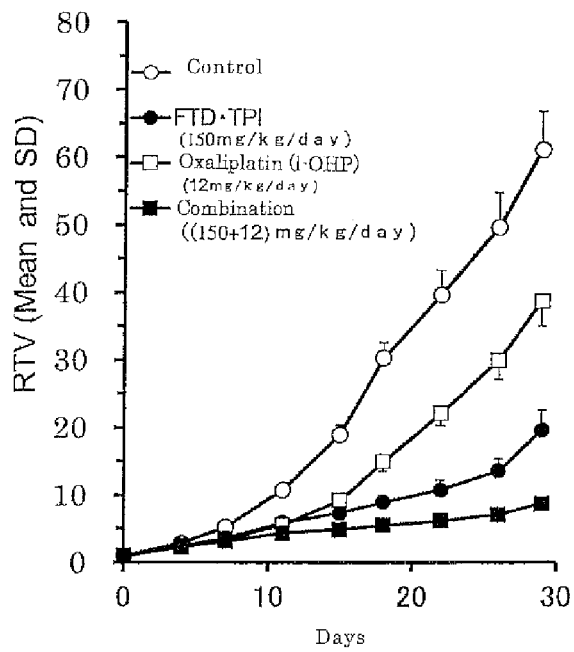
FIG. 10 is a view showing anti-tumor effects in mice having received the FTD•TPI combination drug (a molar ratio of FTD and TPI of 1:0.5) at a dose of 150 mg/kg/day in terms of FTD in combination with oxaliplatin at a dose of 12 mg/kg/day.

As shown in Table 5 and FIGS. 9 and 10, statistically significantly enhanced anti-tumor effects were observed when the FTD•TPI combination drug was administered at 150 mg/kg/day in terms of FTD and oxaliplatin was administered at 7 to 12 mg/kg/day. The number of days that elapsed until the tumor volume reached 5 times that on Day 0 (RTV5) was determined, and the growth delay effect was evaluated (Cancer Chemother Pharmacol 57: 709-718, 2006; Int J Radiat Oncol Biol Phys 86 (3): 469-76, 2013). In each FTD•TPI combination drug administration group, a statistically significant growth delay effect was observed. In the combination administration groups of the FTD•TPI combination drug and oxaliplatin, no serious body weight reduction (more than 20% reduction) was observed, and side effects were acceptable. A test was performed in the same manner as in the above test except that another colon cancer cell line (HCT-116) was used in place of SW48, and statistically significant enhancement of the anti-tumor effect was similarly observed with no serious body weight reduction.

Example 3-3: Combination Use of FTD•TPI Combination Drug and Oxaliplatin (Gastric Cancer)

In a similar manner to that in Example 1, to BALB/cA Jcl-nu mice to which a human gastric cancer cell line (MKN74) was transplanted, the FTD•TPI combination drug or oxaliplatin alone, or a combination of the two was administered, and enhancement of the anti-tumor effect was examined.

The FTD•TPI combination drug (a mixture of FTD and TPI at a molar ratio of 1:0.5) was prepared for administration at a dose of 150 mg/kg/day in terms of FTD. Oxaliplatin (Eloxatin, Sanofi-Aventis) was prepared for administration at doses of 7 and 12 mg/kg/day. The FTD•TPI combination drug was orally administered on Days 1 to 14 consecutively, and oxaliplatin was administered through the tail vein on Day 1 and Day 8. In the combination administration groups, the doses and administration schedules of the FTD•TPI combination drug and oxaliplatin were the same as those of the corresponding monotherapy groups. The TV and body weight of each group were measured on Days 3, 7, 11, 15, 18, 22, 25, and 29, and the anti-tumor effect and side effects were evaluated. The results of the groups on Day 29 are shown in Table 6.

TABLE 6

| Group | Dose (mg/kg/day) | RTV[a] (mean ± SD) | IR[b] (%) | RTV5[c] (days) |
|---|---|---|---|---|
| Control | — | 15.97 ± 0.73 | — | 12.2 ± 0.3 |
| FTD-TPI | 150 | 7.95 ± 0.38* | 50.2 | 21.5 ± 1.0$ |
| Oxaliplatin | 7 | 12.67 ± 0.74 | 20.7 | 15.8 ± 0.6$ |
| (l-OHP) | 12 | 10.25 ± 0.87* | 35.8 | 18.5 ± 0.8$ |
| Combination | 150 + 7 | 4.95 ± 0.44*,# | 69.0 | 28.4 <$,& |
|  | 150 + 12 | 3.78 ± 0.53*,# | 76.3 | 29.0 <$,& |

*$P < 0.001$ vs. Control using two-sided Aspin-Welch t-test.
$P < 0.001$ by closed testing procedure using two-sided Aspin-Welch t-test.
$$P < 0.001$ vs. Control using Log-rank test.
&$P < 0.001$ vs. either monotherapy using Log-rank test.
[a]Relative tumor volume (RTV) on Day 29 was calculated as the ratio of TV on Day 29 to that on Day 0 according to the following formula: RTV = (TV on Day 29)/(TV on Day 0)
[b]Tumor growth inhibition rate (IR) on Day 29 on the basis of RTV was calculated according to the following formula: IR (%) = [1 − (mean RTV of the treated group)/(mean RTV of the control group)] × 100
[c]The period, RTV reaches 5

Figure 11:
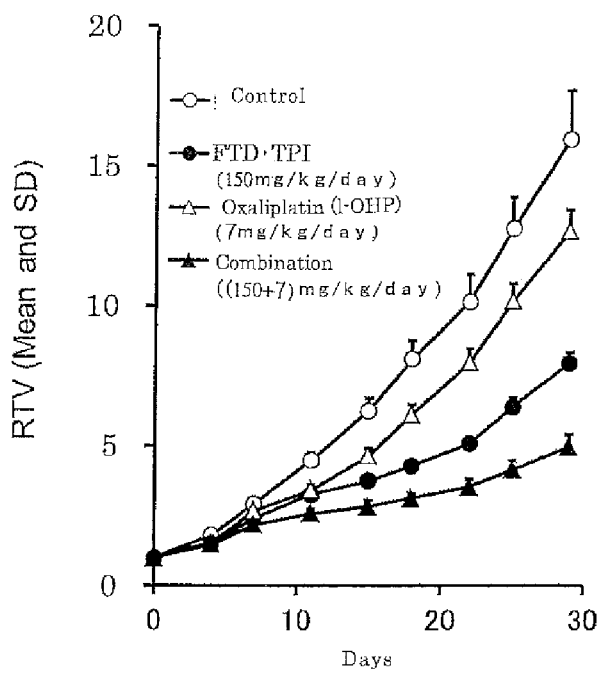
FIG. 11 is a view showing anti-tumor effects in mice having received the FTD•TPI combination drug (a molar ratio of FTD and TPI of 1:0.5) at a dose of 150 mg/kg/day in terms of FTD in combination with oxaliplatin at a dose of 7 mg/kg/day.
Figure 12:
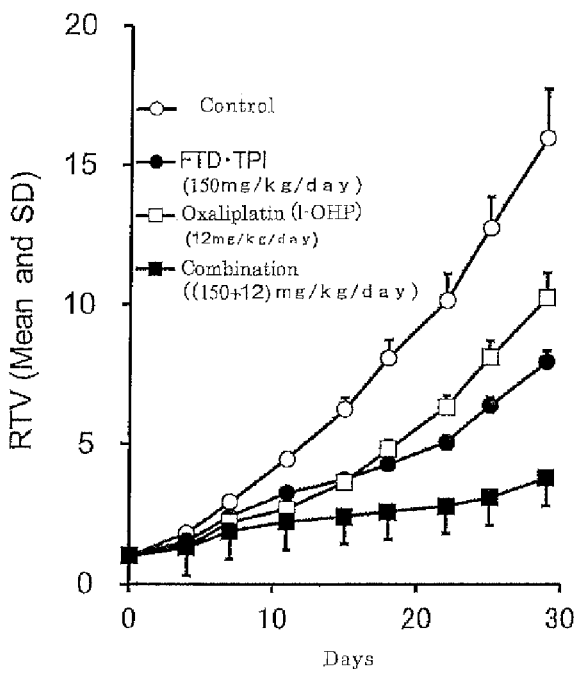
FIG. 12 is a view showing anti-tumor effects in mice having received the FTD•TPI combination drug (a molar ratio of FTD and TPI of 1:0.5) at a dose of 150 mg/kg/day in terms of FTD in combination with oxaliplatin at a dose of 12 mg/kg/day.

As shown in Table 6 and FIGS. 11 and 12, statistically significantly enhanced anti-tumor effects were observed when the FTD•TPI combination drug was administered at 150 mg/kg/day in terms of FTD and oxaliplatin was administered at 7 to 12 mg/kg/day. The number of days that elapsed until the tumor volume reached 5 times that on Day 0 (RTV5) was determined, and the growth delay effect was evaluated. In each FTD•TPI combination drug administration group, a statistically significant growth delay effect was observed. In the combination administration groups of the FTD•TPI combination drug and oxaliplatin, no serious body weight reduction (more than 20% reduction) was observed, and side effects were acceptable.

As shown in Reference Examples, the recommended dose of the FTD•TPI combination drug for use in monotherapy is 150 mg/kg/day (in terms of FTD), and the recommended dose of oxaliplatin for use in monotherapy is 12 mg/kg/day. This indicates that a marked enhancement of the anti-tumor effect was observed when the FTD•TPI combination drug was administered at 100% of the recommended dose for use in monotherapy and oxaliplatin was administered at 58 to 100% of the recommended dose for use in monotherapy.

Example 3-4: Combination Use of FTD•TPI Combination Drug and Oxaliplatin (Gastric Cancer)

In a similar manner to that in Example 1, to BALB/cA Jcl-nu mice to which a human gastric cancer cell line (MKN74/5-FU) that is a 5-FU resistant cell line had been transplanted, the FTD•TPI combination drug or oxaliplatin alone, or a combination of the two was administered, and enhancement of the anti-tumor effect was examined.

The FTD•TPI combination drug (a mixture of FTD and TPI at a molar ratio of 1:0.5) was prepared for administration at a dose of 150 mg/kg/day in terms of FTD. Oxaliplatin (Eloxatin, Sanofi-Aventis) was prepared for administration at doses of 7 and 12 mg/kg/day. The FTD•TPI combination drug was orally administered on Days 1 to 14 consecutively, and oxaliplatin was administered through the tail vein on Day 1 and Day 8. In the combination administration groups, the doses and administration schedules of the FTD•TPI combination drug and oxaliplatin were the same as those of the corresponding monotherapy groups. The TV and body weight of each group were measured on Days 3, 7, 11, 15, 18, 22, 25, and 29, and the anti-tumor effect and side effects were evaluated. The results of the groups on Day 29 are shown in Table 7.

TABLE 7

| Group | Dose (mg/kg/day) | RTV[a] (mean ± SD) | IR[b] (%) | RTV5[c] (days) |
|---|---|---|---|---|
| Control | — | 16.94 ± 1.75 | — | 13.0 ± 0.7 |
| FTD·TPI | 150 | 6.93 ± 0.63* | 59.1 | 22.3 ± 1.5$ |
| Oxaliplatin | 7 | 11.23 ± 1.60* | 33.7 | 18.6 ± 1.4$ |
| (l-OHP) | 12 | 10.08 ± 1.77* | 40.5 | 20.1 ± 1.3$ |
| Combination | 150 + 7 | 4.65 ± 0.56*,# | 72.6 | 28.7 <$,& |
|  | 150 + 12 | 3.42 ± 0.424*,# | 79.8 | 29.0 <$,& |

*P < 0.001 vs. Control using two-sided Aspin-Welch t-test.
P < 0.001 by closed testing procedure using two-sided Aspin-Welch t-test.
$P < 0.001 vs. Control using Log-rank test
&P < 0.001 vs. either monotherapy using Log-rank test.
[a]Relative tumor volume (RTV) on Day 29 was calculated as the ratio of TV on Day 29 to that on Day 0 according to the following formula: RTV = (TV on Day 29)/(TV on Day 0)
[b]Tumor growth inhibition rate (IR) on Day 29 on the basis of RTV was calculated according to the following formula: IR (%) = [1 − (mean RTV of the treated group)/(mean RTV of the control group)] × 100
[c]The period, RTV reaches 5

Figure 13:
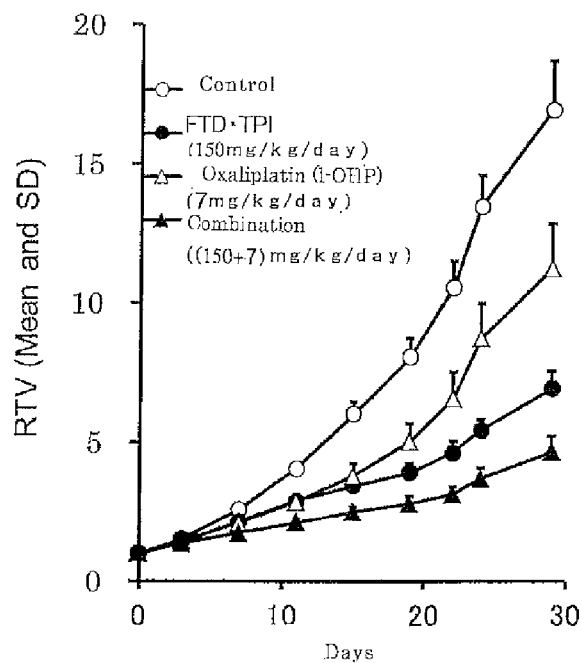
FIG. 13 is a view showing anti-tumor effects in mice having received the FTD•TPI combination drug (a molar ratio of FTD and TPI of 1:0.5) at a dose of 150 mg/kg/day in terms of FTD in combination with oxaliplatin at a dose of 7 mg/kg/day.
Figure 14:
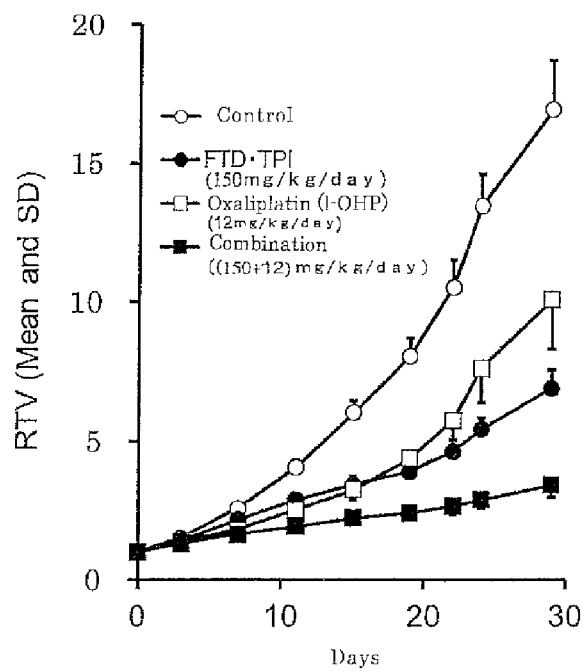
FIG. 14 is a view showing anti-tumor effects in mice having received the FTD•TPI combination drug (a molar ratio of FTD and TPI of 1:0.5) at a dose of 150 mg/kg/day in terms of FTD in combination with oxaliplatin at a dose of 12 mg/kg/day.

As shown in Table 7 and FIGS. 13 and 14, statistically significantly enhanced anti-tumor effects were observed when the FTD•TPI combination drug was administered at 150 mg/kg/day in terms of FTD and oxaliplatin was administered at 7 to 12 mg/kg/day. The number of days that elapsed until the tumor volume reached 5 times that on Day 0 (RTV5) was determined, and the growth delay effect was evaluated. In each FTD•TPI combination drug administration group, a statistically significant growth delay effect was observed. In the combination administration groups of the FTD•TPI combination drug and oxaliplatin, no serious body weight reduction (more than 20% reduction) was observed, and side effects were acceptable. A test was performed in the same manner as in the above test except that another gastric cancer cell line (SC-2) was used in place of MKN74/5-FU, and statistically significant enhancement of the anti-tumor effect was similarly observed with no serious body weight reduction.

As shown in Reference Examples, the recommended dose of the FTD•TPI combination drug for use in monotherapy is 150 mg/kg/day (in terms of FTD), and the recommended dose of oxaliplatin for use in monotherapy is 12 mg/kg/day. This indicates that a marked enhancement of the anti-tumor effect was observed when the FTD•TPI combination drug was administered at 100% of the recommended dose for use in monotherapy and oxaliplatin was administered at 58 to 100% of the recommended dose for use in monotherapy.

As shown in Examples 1 to 3-4, it was ascertained that the anti-tumor effect is significantly enhanced with side effects being suppressed when the FTD•TPI combination drug is administered at 50 to 100% of the recommended dose for use in monotherapy and the anti-tumor platinum complex is administered at 50 to 100% of the recommended dose for use in monotherapy. As shown in Reference Example 1, it is ascertained that the life span increasing effect in the FTD•TPI combination drug administration groups at 300 to 450 mg/kg/day exceeded that in the group at 75 mg/kg/day, at which an enhancement of the anti-tumor effect by combination administration with the anti-tumor platinum complex was observed as shown in the above examples. It is thus suggested that a significant enhancement effect on the anti-tumor effect is exerted when the FTD•TPI combination drug is administered at 75 to 450 mg/kg/day (corresponding to 50 to 300% of the recommended dose for use in monotherapy) in combination with the anti-tumor platinum complex at 50 to 100% of the recommended dose for use in monotherapy. As shown in Example 3-3 and Example 3-4, it was ascertained that the anti-tumor agent of the present invention similarly exerts excellent effect on the cancer that has become resistant to 5-FU due to treatment with 5-FU.

The present invention is not limited to the above-mentioned embodiments and examples and can be variously modified within the scope of claims. The technical scope of the present invention includes embodiments obtained by appropriate combination of technical means disclosed in different embodiments of the present invention. All the academic literature and patent literature disclosed herein are incorporated herein by reference.

The invention claimed is:

1. A method for treating a tumor in a mammal comprising:
    administering an anti-tumor platinum complex and a combination drug containing trifluridine and tipiracil hydrochloride at a molar ratio of 1:0.5, in combination to the mammal,
    wherein a daily dose of the combination drug on an administration day of the combination drug is 50 to 100% of a recommended dose of the combination drug for use in monotherapy, and a daily dose of the anti-tumor platinum complex on an administration day of the anti-tumor platinum complex is 50 to 100% of a recommended dose of the anti-tumor platinum complex for use in monotherapy, wherein the anti-tumor platinum complex is cisplatin, carboplatin, or oxaliplatin.

2. The method according to claim 1, wherein a daily dose of the combination drug on an administration day of the combination drug is 35 to 70 mg/m$^2$/day.

3. The method according to claim 1, wherein a daily dose of cisplatin on an administration day of cisplatin is 45 to 90 mg/m$^2$/day.

4. The method according to claim 1, wherein a daily dose of carboplatin on an administration day of carboplatin is 200 to 400 mg/m$^2$/day.

5. The method according to claim 1, wherein a daily dose of oxaliplatin on an administration day of oxaliplatin is 65 to 130 mg/m$^2$/day.

6. The method according to claim 1, wherein a target cancer is digestive cancer or lung cancer.

7. The method according to claim 1, wherein a target cancer is colorectal cancer, gastric cancer, or lung cancer.

8. A method selected from the group consisting of:
a method of enhancing an anti-tumor effect of an anti-tumor platinum complex, the method comprising: administering an anti-tumor agent consisting of a combination drug containing trifluridine and tipiracil hydrochloride at a molar ratio of 1:0.5 to a mammal;
a method of enhancing an anti-tumor effect of a combination drug containing trifluridine and tipiracil hydrochloride at a molar ratio of 1:0.5, the method comprising: administering an anti-tumor agent consisting of an anti-tumor platinum complex to a mammal;
a method for treating a cancer patient having received an anti-tumor platinum complex, the method comprising: administering an anti-tumor agent consisting of a combination drug containing trifluridine and tipiracil hydrochloride at a molar ratio of 1:0.5 to the cancer patient; and
a method for treating a cancer patient having received a combination drug containing trifluridine and tipiracil hydrochloride at a molar ratio of 1:0.5, the method comprising: administering an anti-tumor agent consisting of an anti-tumor platinum complex to the cancer patient,
wherein a daily dose of the combination drug on an administration day of the combination drug is 50 to 100% of a recommended dose of the combination drug for use in monotherapy, and a daily dose of the anti-tumor platinum complex on an administration day of the anti-tumor platinum complex is 50 to 100% of a recommended dose of the anti-tumor platinum complex for use in monotherapy,
wherein the anti-tumor platinum complex is cisplatin, carboplatin, or oxaliplatin.

* * * * *